United States Patent [19]

Kreckel et al.

[11] Patent Number: 5,061,535
[45] Date of Patent: Oct. 29, 1991

[54] PATTERNED SILICONE RELEASE COATED ARTICLE

[75] Inventors: Karl-Werner Kreckel; Dieter Jung; Egbert Von Jakusch, all of St. Paul, Minn.

[73] Assignee: Minnesota Mining and Manufacturing Company, St. Paul, Minn.

[21] Appl. No.: 545,035

[22] Filed: Jun. 28, 1990

[51] Int. Cl.$^5$ .................................................. B32B 9/00
[52] U.S. Cl. ........................................ 428/42; 428/40; 428/195; 428/446; 428/906; 428/913; 296/93
[58] Field of Search ................. 428/195, 913, 40, 446, 428/906, 42; 296/93

[56] References Cited

U.S. PATENT DOCUMENTS

| | | | |
|---|---|---|---|
| 3,328,482 | 6/1967 | Northrup | 260/825 |
| 3,503,782 | 3/1970 | Ayres | 117/45 |
| 3,527,659 | 9/1970 | Kell | 117/45 |
| 3,741,786 | 6/1973 | Torrey | 117/3.1 |
| 4,208,504 | 6/1980 | Hockemeyer et al. | 528/15 |
| 4,397,905 | 8/1983 | Dettner et al. | 428/40 |
| 4,842,902 | 6/1989 | Brown et al. | 428/40 |

FOREIGN PATENT DOCUMENTS

| | | |
|---|---|---|
| 885746 | 6/1949 | Fed. Rep. of Germany . |
| 3727078 | 2/1989 | Fed. Rep. of Germany . |
| 2209148 | 5/1989 | United Kingdom . |

Primary Examiner—Patrick J. Ryan
Assistant Examiner—Elizabeth Evans
Attorney, Agent, or Firm—Gary L. Griswold; Walter N. Kirn; Douglas E. Reedich

[57] ABSTRACT

A primerless article comprising a substrate, having coated on at least a portion thereof, at least the agent forms a definite geometric pattern consisting of discrete islands and bridges, the islands having dimensions of from about 0.25 mm by 0.25 mm to about 4 mm by 4 mm, the bridges forming a grid, each of the bridges having a width of from about 0.25 mm to about 0.75 mm.

13 Claims, 2 Drawing Sheets

PATTERNED SILICONE RELEASE COATED ARTICLE

FIELD OF THE INVENTION

The invention relates to a substrate which has coated to at least a portion thereof, at least one release agent, wherein the release agent forms a definite geometric pattern.

BACKGROUND OF THE INVENTION

Silicone release agents are well known in the art. Numerous silicones are commercially available, as are liners coated with a layer of silicone. However, these silicones have various drawbacks including controlling the amount of release desirable. Frequently, silicones provides what is known in the art as "premium release", meaning that they exhibit extremely low release values, i.e., 4-60 g/inch of width. These low values are not always desirable, especially for release coatings to be used on the back surfaces of adhesive tapes. This type of back surface coating is known as "low adhesion backsize" or LAB. A controlled release having a value of from 60 to about 2000 g/inch of width to the adhesive is often desired, so that the tape will not prematurely unwind. Silicones are available in both solvent curable, and uv-curable systems. Many nonsilicone polymers such as urethanes are used as LABs because of their higher release force than the silicones. Various modifications of silicones have been attempted for use in adhesive tapes, such as binding them with polymers having higher releases, as in U.S. Pat. Nos. 3,3288,482, 3,527,659 and the like.

Pattern release coatings have been of interest for many years for the goal of controlling release in silicones. In DE-PS 8 55 746, the idea of making a release coating which formed a pattern was disclosed. However, no method for accomplishing the pattern coating was disclosed, nor exemplified. Likewise, UK Patent Application GB 2,209,148 A, published May 4, 1989, discloses a two-layer self-adhesive label having a self-adhesive base which provides a non-adherent area. The nonadherent area is described as printed with a pattern UV cured release panel. However, no method for making such a pattern is disclosed or claimed.

In U.S. Pat. No. 3,503,782, a differential release paper is made by applying a full coating of a first release agent, and a second partial coating of a differing release agent. It is stated that the second coating may be provided in the form of a pattern. In this manner, the surface is provided with a variable release force. However, this requires the complete coating of the surface with one release agent, typically requiring several processing steps and waste of a certain amount of silicone release agent which is under area covered by the second agent.

In DE 3727 078 A1, Beiersdorf, published Feb. 23, 1989, it is disclosed that the problems of making and using this type of coating have never been resolved. It is disclosed in this publication that two layer screen-printed silicone release coatings may be made on a substrate by priming the substrate with a commercial primer, known to have a low release value. Primers disclosed include isocyanate crosslinked polyvinyl acetate, and solutions of chromium stearate complexes mixed with polyvinyl alcohol. The silicone may then be overcoated onto the primer. The silicone is coated using a screen with a sieve size of 10-450 mesh, and typically covers 20-80% of the surface of the primer.

Thus, all of the patterned release liners for which methods of manufacture are disclosed above, have required the use of a primer, or second fully coated layer of release agent.

Processes are also known for pattern printing of other compounds onto substrates, i.e., adhesives. In U.S. Pat. No. 3,741,786, pressure-sensitive adhesive transfer tapes are disclosed having a plurality of substantially non-contiguous raised pressure-sensitive adhesive segments. This construction is disclosed to allow the pressure-sensitive segments to be transferred.

An objective of the present invention is to provide a release article having a patterned coating for use with adhesive tapes and other applications which does not require the use of a primer with the silicone release agent.

Another objective of the present invention is to provide a plurality of articles having smooth controlled release varying from about 20 g/inch to well over 500 g/inch.

SUMMARY OF THE INVENTION

The invention provides a primerless release article comprising a substrate, having coated on at least a portion thereof, at least one layer of a printable silicone release agent, wherein said agent forms a definite geometric pattern consisting of discrete islands and bridges, said islands having dimensions of from about 0.25 mm by 0.25 mm to about 4 mm by 4 mm, said bridges forming a grid, each bridge having a width of from about 0.25 mm to about 1.0 mm.

More specifically, the invention provides two different types of primerless release articles, one being the negative of the other.

The invention provides one type of primerless release article comprising a substrate, and coated on at least a portion thereof, at least one layer of a printable silicone release agent, wherein said agent forms a definite geometric pattern consisting of discrete coated islands and uncoated bridges, said coated islands having dimensions of from about 0.25 mm by 0.25 mm to about 4 mm by 4 mm, said uncoated bridges forming a grid, each bridge having a width of from about 0.25 mm to about 1.00 mm.

The invention also provides a second type of primerless release article comprising a substrate, and coated on at least a portion thereof, at least one layer of a printable silicone release agent, wherein said agent forms a definite geometric pattern consisting of discrete uncoated islands and coated bridges, said uncoated islands having dimensions of from about 0.25 mm by 0.25 mm to about 4 mm by 4 mm, said coated bridges forming a grid, each bridge having a width of from about 0.25 mm to about 1.0 mm.

As used herein, the ensuing terms have the correlative meanings.

1. The term "island" means a discrete area having a defined geometric shape.
2. The term "bridge" means a discrete columnar area which may intersect with other bridges to form a grid pattern.
3. The term "grid" means a pattern of interconnected bridges emanating from differing points, forming and surrounding roughly equivalent geometric islands.

DETAILED DESCRIPTION OF THE INVENTION

Figure 1:
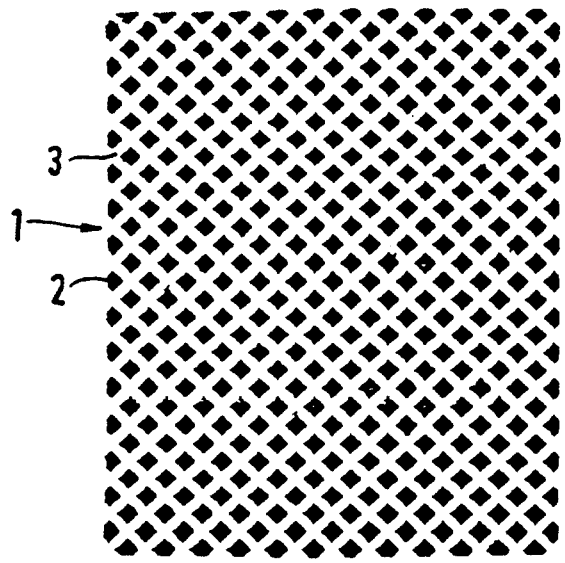
FIG. 1 shows a release article of the invention. The surface of the substrate 1, is coated with a silicone release agent in a pattern characterized by coated areas, or islands 2, each island having an edge area of 3 mm and uncoated bridges 3 forming a grid, each bridge having a width of 1 mm. The total percentage of the surface area which is siliconized is 56%.
Figure 2:
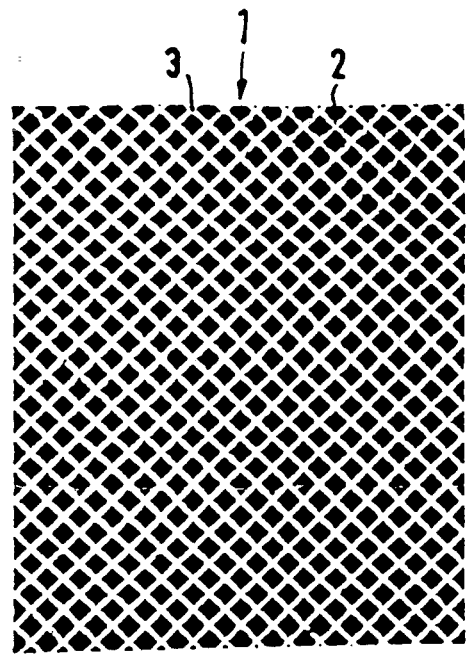
FIG. 2 shows another release article of the invention. The surface of the substrate 1, is coated with a silicone release agent in a pattern characterized by coated areas 2 and uncoated bridges 3 forming a grid. The islands are similar in size to those of FIG. 1, the bridges have a width of 0.5 mm, narrower than those of FIG. 1. The total percentage of the surface area which is siliconized is 72%.
Figure 3:
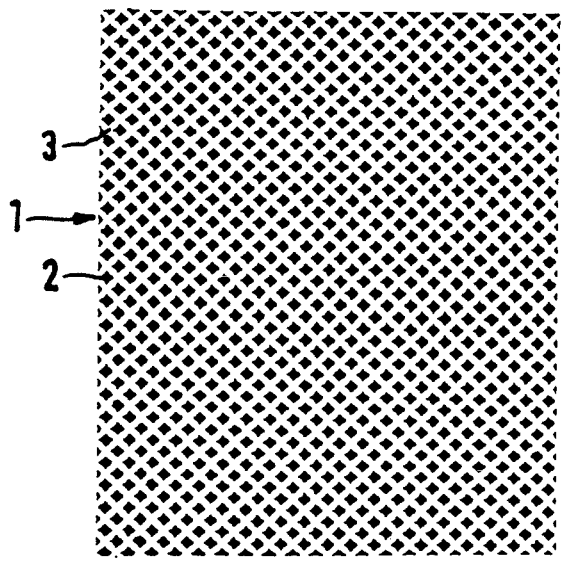
FIG. 3 shows another release article of the invention. The surface of the substrate 1, is coated with a silicone release agent in a pattern characterized by coated areas 2 and uncoated bridges 3, forming a grid. This pattern is characterized by smaller islands than FIGS. 1 and 2, each island having an edge area of 2 mm, and each bridge width being 0.5 mm. The total percentage of the surface area which is siliconized is 64%.
Figure 4:
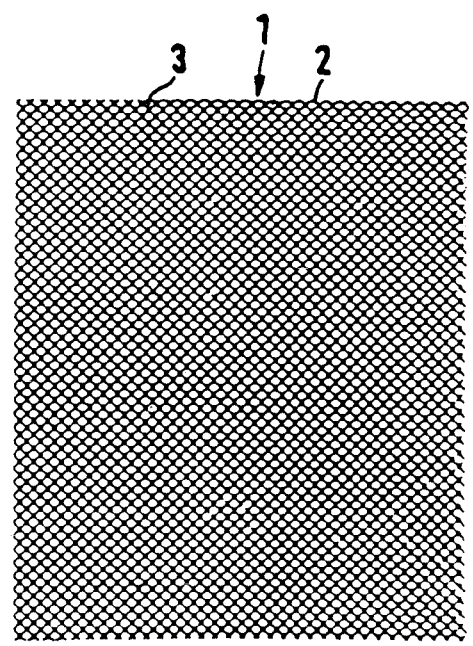
FIG. 4 shows a second type of release article of the invention. The surface of the substrate 1, is coated by a silicone release agent in a pattern characterized by uncoated islands 3 each uncoated island having an edge area of 1 mm and coated bridges forming a grid 2, each bridge having a width of 0.75 mm. The total percentage of the surface area which is siliconized is 33%.
Figure 5:
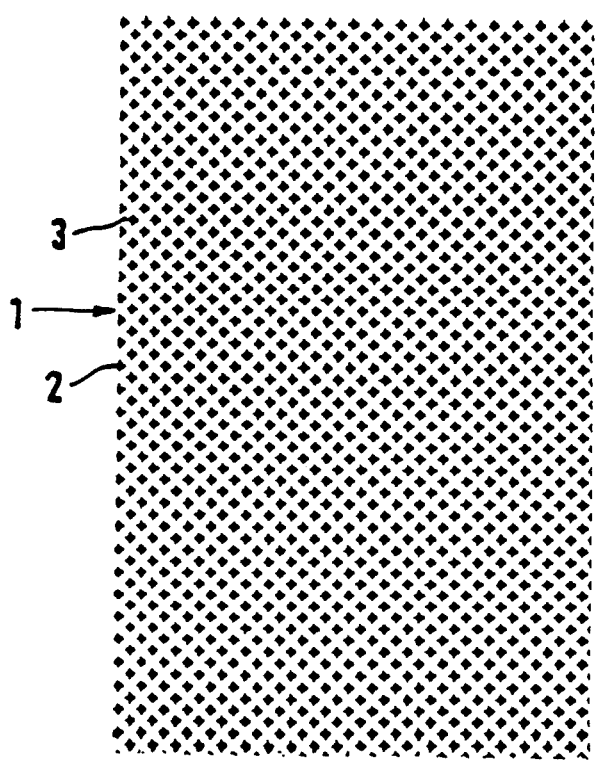
FIG. 5 shows another release article of the invention. The surface of the substrate 1 is coated with a silicone release agent in a pattern characterized by coated islands 2 and uncoated bridges 3, forming a grid. This patterns characterized by smaller islands than FIGS. 1 and 2, each island having a edge area of 2 mm, and bridge width being 0.75 mm. The total percentage of the surface area which is siliconized is 53%.
Figure 6:
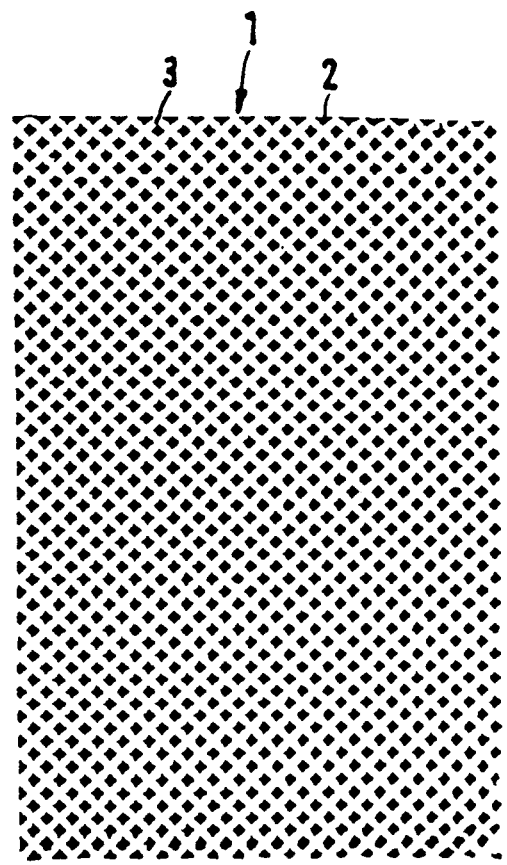
FIG. 6 shows another release article of the invention. The surface of the substrate 1, is coated with a silicone release agent in a pattern characterized by coated islands 2 and uncoated bridges 3, forming a grid. This pattern is characterized by square islands having an edge area of 1.75 mm, and each bridge width being 0.75 mm. The total percentage of the surface area which is siliconized is 49%.

By "primerless" as used in the instant specification and claims is meant that the release article does not contain a layer of polymeric material between the film substrate and the layer of silicone release agent which serves to enhance the bonding of the silicone release agent to the film substrate. "Primerless", however, does not exclude, for example, corona or flame treatment of the film substrate prior to application of the silicone release agent.

Release articles of the invention are particularly useful when release force values in excess of 100 g/inch are desired.

Silicone release agents useful in articles of the invention include a wide variety of organopolysiloxanes. The compositions are preferably, but not necessarily, high molecular weight silicone polymers or copolymers. Some useful examples include both ultraviolet radiation cured and solvent coated silicones such as polyorganosiloxanes, including polydimethylsiloxanes, epoxypolysiloxanes, and the like.

In preferred articles, a solvent-free crosslinkable silicone system is used, such as epoxy functional diorganopolysiloxanes, in which up to 20% of the groups are epoxy functional groups as described in U.S. Pat. No. 4,547,431. Also useful are the radiation curable coatings described in U.S. Pat. No. 4,576,999 wherein there is disclosed precrosslinking polyorganosiloxane containing units of

where R is $C_{(1-3)}$ alkyl and G is independently $C_{(1-3)}$ alkyl, an epoxy-functional organic radical of 2 to 20 carbon atoms, or an acrylic functional radical of 2–20 carbon atoms with at least one unit being epoxy or acrylic functional.

Also useful are epoxy substituted polysiloxanes having the formula

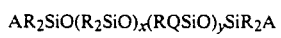

wherein $R_2$ is a monovalent hydrocarbon or halogenated hydrocarbon group having from 1 to 10 carbon atoms, A is R or Q, and Q is a group with the formula

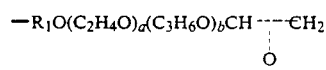

$R_1$ is an alkylene group having from 3 to 5 carbon atoms, a has an average value of 0 to 300 and b has an average value of 0 to 30, a+b has an average value of 2 to 60, x has an average value of 1 to 500, and y has an average value of 0 to 100, and each molecule contains at least one Q group.

Also useful are combinations of vinyl endblocked diorganopolysiloxanes in which from 3 to 30 mole percent of the nonterminal siloxane units and at least 50 mole percent of the remaining organic radicals on the siloxane units are methyl radicals, and organopolysiloxanes which have at least 3 Si-bonded hydrogen atoms per molecule as disclosed in U.S. Pat. No. 4,208,504.

The release agent exhibits a definite geometric pattern consisting of discrete islands and bridges on the substrate, wherein the islands have dimensions of from about 0.25 mm by 0.25 mm to about 4 mm by 4 mm, and the uncoated bridges form a grid, each bridge having a width of from about 0.25 mm to about 1.0 mm. In preferred articles of the invention, the islands have dimensions of from about 0.50 mm by 0.50 mm to about 3 mm by 3 mm. Where a high tack adhesive is used, the bridges must be no wider than 0.75 mm, preferably from about 0.25 mm to about 0.50 mm.

The islands present in the pattern, whether coated areas, or uncoated areas, may be square, circular, triangular, elliptic, rhombic, or other defined geometric shape. The bridges then form a related grid. For example, where the islands are circular, the bridges are narrow between adjacent circles, and the intersection of the bridges is enlarged; where the islands are square, the bridges form diagonally opposed equal lines.

The particular geometric shape used depends on the release values desired for the release article, the nature of the adhesive which it will contact, and the type of substrate.

If desired, a given substrate may have two or more different patterns of silicone release agent coated thereon to provide an article which exhibits varying release properties over its surface. For example, a diaper tape may be fashioned to adhere more aggressively in a particular region than another.

Useful substrates are polymeric film, saturated papers, and glassine paper. Examples of thermoplastic films are such as polyolefins, foils or polyester. Saturated and glassine papers are papers that are treated to increase the internal adhesion of the paper so that it does not split or delaminate when the release coated paper is removed from a pressure sensitive adhesive coating.

The printing of the release coat or coats may be carried out in a single printing step by any suitable printing technique. The pattern is coated on a roll-coater having a plurality of transfer rolls equiped with feed devices which meter the release agent in accurately defined weights onto the outer roll surface of the coater roll. The coater rolls are fitted with an embossed outer surface corresponding to the pattern to be printed onto the substrate. The solvent-free systems, e.g. uv-curable materials are especially print-technology applicable.

For certain polymeric substrates, such as polypropylene, the surface must be modified by corona treatment or flame treatment to improve the adhesion of the release coating to the substrate. About 38 dynes/cm (or the equivalent in N/cm) is the minimum surface tension of polypropylene to obtain a sufficiently good bond between the silicone and the substrate.

Articles of the invention are useful for rolled adhesive tape (e.g., diaper tapes and foam weather stripping tapes), adhesive transfer tapes, double-coated tapes, abrasive articles, and bandages for transcutaneous administration of a microemulsion medicament. Such a device contains an absorbant material placed in a stamped out reservoir which intersects a piece of closed-cell polyethylene foam. The medicament is contained in the absorbant material. The polyethylene foam piece is covered by a protective polyester foil for storage. This foil is coated with the patterned silicone coating of the invention.

The following tests have been used for evaluating articles of the invention. All weight, ratios, and percentages herein are by weight unless otherwise specifically noted.

GLOSSARY OF TERMS

1. Tape X—A standard pressure-sensitive adhesive tape having an acrylic pressure-sensitive adhesive as disclosed in U.S. Pat. Re. No. 24,906, i.e., a 95.5:4.5 isooctyl acrylate: acrylic acid adhesive coated onto a 0.5 mm polyester film.
2. Tape Y—A solvent based rubber resin pressure sensitive adhesive tape having 35% Kraton TM 1107, available from Shell Chemical Company, 16.5% Wingtack TM 10, available from Goodyear Chemical Company; and 46.5% Wingtack TM Plus, available from Goodyear Chemical Company, dispersed in a solvent mixture of 4:1 toluene:heptane, and coated onto a 90 mm cast polypropylene film.
3. Tape Z—A solvent based rubber resin pressure sensitive adhesive having 33% Kraton TM 1107; 44% Escorez TM 1310, available from Exxon Chemical Company; 22% Zonarez TM A25, available from Arizona Chemical and 1% Irganox TM 1076 Antioxidant, available from Ciba Geigy, dispersed in a mixture of 4:1 toluene:heptane and coated onto a polyethylene coated paper.

TEST METHODS

RELEASE VALUE TEST PROCEDURE

A pressure-sensitive adhesive tape is pressed against the surface of a release coated substrate using two passes of a 2 Kg rubber roller to produce a laminate. The laminate was cut into 25 mm × 250 mm strips and attached, substrate side down, to a smooth stainless steel panel. The release value is the force, in grams, required to pull the pressure-sensitive adhesive tape with adhesive adhered thereto away from the release coated substrate at an angle of 180° and a pulling speed of 300 mm/min.

HEAT AGED RELEASE VALUE TEST

A laminate of a pressure-sensitive adhesive tape and release coated substrate was prepared as described above and heated in an oven at 70° C. under a constant load of 20 grams per square centimeter for 20 hours. After this time, the laminate was removed from the oven, allowed to cool for at least 10 minutes at room temperature, and within 2 hours after removal from the oven, the force required to pull the pressure sensitive tape with adhesive adhered thereto away from the release coated substrate was measured as described above in the test for Release Value.

READHESION TEST

A 25×250 mm strip of pressure sensitive tape, as removed from the release coated substrate, was pressed to the surface of a bright annealed stainless steel panel using two passes of a 2 Kg rubber roller. The readhesion value is the force, in Newtons/25 mm, required to pull the tape from the panel surface at an angle of 180° and a stripping speed of 300 mm/min.

EXAMPLES

EXAMPLE 1

An epoxy silicone having an epoxy equivalent weight of 865 is prepared as described in U.S. Pat. No. 4,822,687, and coated onto an 0.085 mm cast corona treated polypropylene film in an island having 1 mm × 1 mm islands and separated by bridges of 0.375 mm. The silicone is cured as described in the reference. The sample was tested according to the test methods for Release Value, Heat-Aged Release Value, and Readhesion, described above and the test results are summarized in Table 1.

EXAMPLES 2–10

Examples 2–10 were prepared as described in Example 1 except that the island and bridge sizes were changed as indicated in Table 1.

EXAMPLES 12–14

Example 12–14 were made as described in Example 1 with island and bridge sizes as shown in Table 1. Test Tape Y was used in the Release Value Test.

EXAMPLES 115-17

Examples 15-17 were made as using an epoxy silicone having an Epoxy Equivalent Weight of 445. The epoxy silicone was made as described in U.S. Pat. No. 4,822,687. The island size and bridge widths are shown in Table 1.

EXAMPLES 18-30

Examples 18-30 were made by coating Wacker-Chemie "VP-1530", available from Wacker-Chemie GmbH in the island sizes and bridge width as indicated in Table 1 and cured under UV light.

EXAMPLES 31-32

Examples 31-32 were made by coating Wacker Dehasive ™ 920, available from Wacker-Chemie GmbH in the island sizes and bridge width as indicated in Table 1 and heat cured.

EXAMPLES 33-35

Examples 33-35 were made as in Example 1 except that the island was coated as a grid with the island sizes indicating the uncoated islands and the bridge sizes indicating the width of the coated bridges forming the grid.

EXAMPLE 36

Example 36 was made as in Example 33 except that the silicone was coated onto a 0.040 mm biaxially oriented polypropylene film.

TABLE I

| Ex | Islands Size-mm | bridge mm | Silicone/ Substrate | Test Tape | Release Value g/25 mm | Heat Aged Release Value g/25 mm | Readhesion Value N/25 mm |
|---|---|---|---|---|---|---|---|
| 1 | 1 × 1 | 0.375 | A | X | 242 | 234 | 13.4 |
| 2 | 1 × 1 | 0.500 | A | X | 312 | 319 | 13.1 |
| 3 | 1 × 1 | 0.625 | A | X | 429 | 452 | 11.4 |
| 4 | 2 × 2 | 0.375 | A | X | 137 | 174 | 11.8 |
| 5 | 2 × 2 | 0.500 | A | X | 139 | 176 | 13.4 |
| 6 | 2 × 2 | 0.625 | A | X | 385 | 450 | 9.9 |
| 7 | 3 × 3 | 0.375 | A | X | 54 | 51 | 14.9 |
| 8 | 3 × 3 | 0.500 | A | X | 79 | 95 | 11.9 |
| 9 | 3 × 3 | 0.625 | A | X | 230 | 261 | 9.8 |
| 10 | 4 × 4 | 0.500 | A | X | 80 | 62 | 16.5 |
| 11 | Comparative* | | A | X | 10 | 15 | 14.5 |
| 12 | 1 × 1 | 0.025 | A | Y | 77 | — | — |
| 13 | 1 × 1 | 0.500 | A | Y | 791 | — | — |
| 14 | 1 × 1 | 0.750 | A | Y | 1507 | — | — |
| 15 | 1 × 1 | 0.025 | B | Y | 533 | — | — |
| 16 | 1 × 1 | 0.500 | B | Y | 1039 | — | — |
| 17 | 1 × 1 | 0.750 | B | Y | 1813 | — | — |
| 18 | 1 × 1 | 0.375 | C | Z | 49 | 349 | 12.1 |
| 19 | 1 × 1 | 0.500 | C | Z | 126 | 648 | 11.5 |
| 20 | 1 × 1 | 0.625 | C | Z | 81 | 360 | 12.0 |
| 21 | 2 × 2 | 0.375 | C | Z | 17 | 138 | 15.3 |
| 22 | 2 × 2 | 0.500 | C | Z | 41 | 211 | 15.4 |
| 23 | 2 × 2 | 0.625 | C | Z | 64 | 392 | 11.5 |
| 24 | 3 × 3 | 0.375 | C | Z | 12 | 87 | 15.9 |
| 25 | 3 × 3 | 0.500 | C | Z | 18 | 109 | 14.9 |
| 26 | 3 × 3 | 0.625 | C | Z | 32 | 161 | 13.7 |
| 27 | Comparative* | | C | Z | 15 | 18 | 17.5 |
| 28 | 2 × 2 | 0.750 | C | #5336 | 495 | 804 | — |
| 29 | 1.75 × 1.75 | 0.750 | C | #5336 | 532 | 968 | — |
| 30 | Comparative* | | C | #5336 | 72 | 91 | — |
| 31 | 2 × 2 | 0.750 | D | #5337 | 1196 | 1826** | 40.5 |
| 32 | Comparative* | | D | #5337 | 740 | 208** | 47.2 |
| 33*** | 1 × 1 | 0.750 | A | X | 41.8 | 54.3 | 10.3 |
| 34*** | .75 × .75 | 0.750 | A | X | 12.5 | 114 | 15.3 |
| 35*** | 1 × 1 | 0.750 | A | Z | 253 | — | — |
| 36*** | 1 × 1 | 0.750 | E | Z | 177 | — | — |

A - Epoxysiloxane with an Epoxy Equivalent Weight of 865 coated onto 0.085 mm thick cast polypropylene
X - Test Tape X.
B - Epoxysiloxane with an Epoxy Equivalent Weight of 445 coated onto 0.089 mm thick cast polypropylene
Y - Test Tape Y.
C - Wacker-Chemie "VP-1530" coated onto 0.085 mm thick cast polypropylene film.
Z - Test Tape Z.
5336 - Foam Tape #5336 available from 3M Company, St. Paul, MN.
5337 - Foam Tape #5337 available from 3M Company, St. Paul, MN.
D - Wacker Dehasive ™ 920 thermally cured silicone coated onto 0.085 mm cast polypropylene film.
E - Epoxysiloxane with an Epoxy Equivalent Weight of 865 coated onto 0.040 thick biaxially oriented polypropylene film.
*Comparative is fully coated with silicone.
**Heat Aged Release Value Test is conducted as described above except that the samples were aged for 7 days at 70° C.
***Grid pattern in which the pattern size indicates the islands which are uncoated and the bridges form the grid which is silicone coated.

What is claimed is:

1. A primerless release article comprising a film substrate, having coated on at least a portion thereof, at least one layer of a printable silicone release agent, wherein said agent forms a definite geometric pattern consisting of discrete islands and bridges, said islands having dimensions of from about 0.25 mm by 0.25 mm to about 4 mm by 4 mm, said bridges forming a grid, each bridge having a width of from about 0.25 mm to about 1.0 mm.

2. A primerless release article comprising a film substrate, having coated on at least a portion thereof, at least one layer of a printable silicone release agent, wherein said agent forms a definite geometric pattern consisting of discrete islands and bridges, said islands having dimensions of from about 0.25 mm by 0.25 mm to about 3 mm by 3 mm, said bridges forming a grid, each bridge having a width of from about 0.25 mm to about 0.75 mm.

3. A primerless release article according to claim 1 wherein said islands are coated with said silicone release agent, and said bridges are uncoated.

4. A primerless release article according to claim 1 wherein said bridges are coated with said silicone release agent, and said islands are uncoated.

5. A primerless release article according to claim 4 wherein said coated islands have dimensions of from about 0.5 mm by 0.5 mm to about 3 mm by 3 mm.

6. A primerless release article according to claim 1 wherein said silicone release agent is uv-curable.

7. A primerless release article according to claim 4 wherein said silicone release agent is a crosslinkable silicone.

8. A primerless release article according to claim 1 wherein said islands are in the form of squares.

9. A primerless release article according to claim 1 wherein said substrate has two or more different patterns of silicone release agent coated thereon to provide an article which exhibits varying release properties over the surface thereof.

10. A primerless release article according to claim 1 in the form of a diaper tape.

11. A primerless release article in the form of an adhesive-coated abrasive articles.

12. A primerless release article in the form of a foam weather stripping tape.

13. A process for providing a primerless release article consisting of coating at least one surface of a substrate with at least one printable silicone release agent in a definite geometric pattern, such that discrete islands and bridges are formed, said islands being coated with said silicone release agent, and said bridges being uncoated.

* * * * *